United States Patent [19]

Jordan

[11] Patent Number: 5,630,871
[45] Date of Patent: May 20, 1997

[54] FILM COATINGS AND FILM COATING COMPOSITIONS BASED ON CELLULOSIC POLYMERS AND LACTOSE

[75] Inventor: Martin P. Jordan, Orpington, England

[73] Assignee: Berwind Pharmaceutical Services, Inc., West Point, Pa.

[21] Appl. No.: 400,134

[22] Filed: Mar. 6, 1995

Related U.S. Application Data

[63] Continuation of Ser. No. 3,604, Jan. 13, 1993, abandoned.

[30] Foreign Application Priority Data

Jan. 17, 1991 [EP] European Pat. Off. .............. 92300406

[51] Int. Cl.$^6$ ...................... C09D 101/00; C09D 101/28
[52] U.S. Cl. .................................. 106/162.7; 106/162.8; 106/162.9
[58] Field of Search .................. 106/163.1, 176, 106/703, 704, 162.7, 162.8, 162.9

[56] References Cited

U.S. PATENT DOCUMENTS

| | | | |
|---|---|---|---|
| 3,751,277 | 8/1973 | Small et al. | 424/361 |
| 4,248,858 | 2/1981 | Guley et al. | 424/21 |
| 4,250,195 | 2/1981 | Cherukuri et al. | 426/5 |
| 4,287,221 | 9/1981 | Tonedachi et al. | 427/3 |
| 4,292,299 | 9/1981 | Suzuki et al. | 424/16 |
| 4,302,440 | 11/1981 | John et al. | 424/35 |
| 4,421,738 | 12/1983 | Yamagiwa et al. | 424/35 |
| 4,652,313 | 3/1987 | Den Boer et al. | 106/289 |
| 4,661,162 | 4/1987 | Kurihara et al. | 106/169 |
| 4,693,750 | 9/1987 | Bauer et al. | 106/163.1 |
| 4,786,511 | 11/1988 | Huzinec et al. | 426/5 |
| 4,790,881 | 12/1988 | Wittwer et al. | 106/189 |
| 4,802,924 | 2/1989 | Woznicki et al. | 427/3 |
| 4,857,337 | 8/1989 | Miller et al. | 424/480 |
| 4,913,919 | 4/1990 | Cornwell et al. | 426/94 |
| 4,983,399 | 1/1991 | Maish | 106/181 |
| 5,098,715 | 3/1992 | McCabe et al. | 424/479 |
| 5,194,464 | 3/1993 | Itoh et al. | 106/178 |

FOREIGN PATENT DOCUMENTS

| | | | |
|---|---|---|---|
| 49-133515 | 5/1973 | Japan . | |
| 51-123815 | 10/1976 | Japan | A61K 8/36 |

*Primary Examiner*—David Brunsman
*Attorney, Agent, or Firm*—John F. A. Earley; John F. A. Earley, III

[57] ABSTRACT

A dry film coating composition for use in coating pharmaceuticals, food, confectionery forms, agricultural seeds, and the like, comprises a cellulosic polymer, and lactose. The composition may include an optional plasticizer, and an optional pigment. A method of coating substrates such as pharmaceutical tablets, food and confectionery forms, agricultural seeds, and the like comprises mixing a cellulosic polymer and lactose into water to form an aqueous coating suspension, spraying the coating suspension onto said substrates to form a film coating on said substrates, and drying the film coating on said substrates. Optionally, a plasticizer and/or pigment may be dispersed into the aqueous coating suspension. The method of making a dry film coating composition for use in coating pharmaceutical tablets, food and confectionery forms, agricultural seeds, and the like, comprises mixing a cellulosic polymer and lactose together to form a dry film coating composition. Optionally, a plasticizer and/or pigment is blended with the cellulosic polymer and lactose. A method of making a dry film coating composition for use in coating pharmaceutical tablets, food and confectionery forms, agricultural seeds, and the like comprises mixing a cellulosic polymer and lactose into water to form an aqueous coating suspension, and spray granulating the aqueous coating suspension to form a dry film coating compositions. Optionally, a plasticizer and/or pigment may be mixed into the aqueous coating suspension. An aqueous coating suspension for coating substrates such as pharmaceutical tablets, food and confectionery forms, agricultural seeds, and the like, comprises a mixture of a cellulosic polymer, lactose, water, and optionally, plasticizer and/or pigment.

19 Claims, No Drawings

FILM COATINGS AND FILM COATING COMPOSITIONS BASED ON CELLULOSIC POLYMERS AND LACTOSE

This is a continuation application, Ser. No. 08/003,604 filed on Jan. 13, 1993, now abandoned.

BACKGROUND OF THE INVENTION

1. Field of the Invention

The present invention relates to the field of aqueous film coating of pharmaceutical, food, confectionery forms, and agricultural products, and is specifically concerned with providing coatings from a combination of a cellulosic polymer and lactose for coating such things as pharmaceutical tablets, pieces of candy, cereals, and agricultural seeds.

2. Description of the Prior Art

Film coating is a process of depositing a thin layer of material onto a substrate. Two goals of film coating substrates such as pharmaceutical tablets and the like are (1) to provide a functional protective barrier covering the outer surface of the substrate, and (2) to provide a pleasing appearance.

The process of film coating pharmaceutical, food, confectionery, and agricultural pieces usually involves rolling the pieces in a pan, or suspending the pieces on a cushion of air, and continuously spraying a fine mist of atomized droplets of a coating suspension onto the pieces, the droplets coalescing on the surface of the pieces to form a film coating.

Coating suspensions having an organic solvent are undesirable since these solvents are often flammable, often toxic, and hazardous to the health of film coating workers. Further, reclaiming organic solvent fumes, which are given off during spraying, from exhaust air ducting systems is expensive and often required by law.

Water-based coating suspensions are desirable to avoid the drawbacks of organic solvent-based coating suspensions. However, a major problem with aqueous coating suspensions is poor adhesion of the film to the substrate.

SUMMARY OF THE INVENTION

A dry film coating composition for use in pharmaceuticals, food, confectionery forms, agricultural seeds, and the like comprises a dry mixture of a cellulosic polymer and lactose. Optionally, the composition may include a plasticizer and/or a pigment.

A method of coating substrates such as pharmaceutical tablets, food and confectionery forms, agricultural seeds, and the like, comprises mixing a cellulosic polymer and lactose into water to form an aqueous coating suspension, spraying the coating suspension onto said substrates to form a film coating on said substrates, and drying the film coating on said substrates.

The invention also includes the coated substrates, such as coated pharmaceutical tablets, and methods of making the dry film coating composition and of making a coating suspension.

Examples of the cellulosic polymer are hydroxypropyl methylcellulose and hydroxypropyl cellulose.

Exemplary of the plasticizer are polyethylene glycol having a molecular weight of 200 to 20,000, propylene glycol, or glycerol.

Any of the pigments heretofore used in making coating dispersions for coating tablets, food, confectionery forms, agricultural seeds, and the like may be used. Examples are FD&C and D&C lakes, titanium dioxide, iron oxides or natural pigments.

The quantity of the cellulosic polymer is within a range of about 11% to about 56% by weight of the dry film coating composition and of the non-water ingredients of the aqueous coating suspension. A range of about 20% to 30% by weight of the dry film coating composition and of the non-water ingredients of the aqueous coating suspension is preferred.

The quantity of the lactose is within a range of about 11% to about 56% by weight of the dry film coating composition and of the non-water ingredients of the aqueous coating suspension. A range of about 25% to 45% by weight of the dry film coating composition and of the non-water ingredients of the aqueous coating suspension is preferred.

The quantity of the plasticizer is within a range of 0% to about 55% by weight of the dry film coating composition and of the non-water ingredients of the aqueous coating suspension. A range of about 5% to 20% by weight of the dry film coating composition and of the non-water ingredients of the aqueous coating suspension is preferred.

The quantity of the pigment is within a range of 0% to about 55% by weight of the dry film coating composition and of the non-water ingredients of the aqueous coating suspension. A range of about 15% to 40% by weight of the dry film coating composition and of the non-water ingredients of the aqueous coating suspension is preferred.

A preferred formula for the present inventive dry film coating composition is:

| COMPONENT | % w/w |
| --- | --- |
| CELLULOSIC POLYMER | 26.80 |
| LACTOSE | 40.20 |
| PLASTICIZER | 8.00 |
| PIGMENT | 25.00 |

The following examples of the invention all disclose formulations which may be mixed into water to form an aqueous coating suspension effective to coat pharmaceutical tablets, food and confectionery pieces, and agricultural seeds. Seeds are advantageously coated to meet various needs, such as color coating for identification purposes, adhesion of various additives, (e.g., pest control agents and inocula), prevention of handling damage, and facilitating the use of mechanical planting equipment. The coated forms include medicinal tablets, vitamin tablets, aspirin tablets, capsules, chewing gum balls, candy pieces, breakfast cereals, and agricultural seeds.

EXAMPLES

The following examples illustrate the invention. All units and percentages used herein are by weight.

EXAMPLE 1

67.00 grams of hydroxypropyl methylcellulose (Methocel E15 made by Dow Chemical Company), 100.50 grams of lactose, 60.00 grams of titanium dioxide, and 2.50 grams of Indigo carmine aluminum lake 14% are loaded into a dry powder blender such as a P.K. blender and mixed vigorously for 25 minutes to form an homogenous mixture. Then, 20.00 grams of a plasticizer, polyethylene glycol 4000 (PEG 4000 made by Union Carbide), is added to the homogenous mixture and gently blended into it.

Optionally, the homogenous mixture containing the plasticizer is granulated using a planetary mixer, such as a Hobart planetary mixer. After the dry film coating composition is loaded into the mixer and the mixer is switched on, sufficient water is slowly added until the composition forms slightly adherent granules. These granules are then passed through a 1–2 mm screen and then dried in a 30' C. oven until the moisture content is below 5%. The composition is then sieved again through a 1–2 mm screen and is then ready for use in a non-dusting, granular form. If not optionally granulated in a planetary mixer, the powder may be milled such as in a hammer mill (Apex Machinery, Dartford, England), for example.

Other methods of granulation which may be used are spray granulation and roller compaction.

The following examples 2 to 17, which show different formulations of the dry film coating composition of the invention, further illustrate the invention. In each example 2 to 17, a dry film coating composition is made using the procedure of Example 1. Methocel E15 and Methocel E50 are hydroxypropyl methylcellulose (HPMC) made by Dow Chemical Company. PEG 200, PEG 400, PEG 4000, PEG 8000, and PEG 20000 are polyethylene glycol made by Union carbide. Klucel EF is hydroxypropyl cellulose made by Hercules Co.

EXAMPLE 2

| COMPONENT | % w/w | grams |
|---|---|---|
| HPMC (Methocel E15) | 20.39 | 50.98 |
| LACTOSE | 30.58 | 76.44 |
| PEG 4000 | 30.00 | 75.00 |
| TiO2 | 18.27 | 45.68 |
| INDIGO CARMINE ALUMINUM LAKE 14% | 0.76 | 1.90 |
| | 100.00 | 250.00 |

EXAMPLE 3

| COMPONENT | % w/w | grams |
|---|---|---|
| HPMC (Methocel E15) | 16.00 | 40.00 |
| LACTOSE | 24.00 | 60.00 |
| PEG 4000 | 14.55 | 36.38 |
| TiO2 | 43.64 | 109.10 |
| INDIGO CARMINE ALUMINUM LAKE 14% | 1.81 | 4.52 |
| | 100.00 | 250.00 |

EXAMPLE 4

| COMPONENT | % w/w | grams |
|---|---|---|
| HPMC (Methocel E15) | 55.83 | 139.57 |
| LACTOSE | 11.17 | 27.93 |
| PEG 4000 | 8.00 | 20.00 |
| TiO2 | 24.00 | 60.00 |
| INDIGO CARMINE ALUMINUM LAKE 14% | 1.00 | 2.50 |
| | 100.00 | 250.00 |

EXAMPLE 5

| COMPONENT | % w/w | grams |
|---|---|---|
| HPMC (Methocel E15) | 11.17 | 27.93 |
| LACTOSE | 55.83 | 139.57 |
| PEG 4000 | 8.00 | 20.00 |
| TiO2 | 24.00 | 60.00 |
| INDIGO CARMINE ALUMINUM LAKE 14% | 1.00 | 2.50 |
| | 100.00 | 250.00 |

EXAMPLE 6

| COMPONENT | % w/w | grams |
|---|---|---|
| HPMC (Methocel E15) | 15.66 | 39.15 |
| LACTOSE | 24.00 | 60.00 |
| PEG 4000 | 5.34 | 13.35 |
| TiO2 | 52.80 | 132.00 |
| INDIGO CARMINE ALUMINUM LAKE 14% | 2.20 | 5.50 |
| | 100.00 | 250.00 |

EXAMPLE 7

| COMPONENT | % w/w | grams |
|---|---|---|
| HPMC (Methocel E15) | 26.80 | 67.00 |
| LACTOSE | 40.20 | 100.50 |
| PEG 4000 | 8.00 | 20.00 |
| IRON OXIDE YELLOW | 25.00 | 62.50 |
| | 100.00 | 250.00 |

EXAMPLE 8

| COMPONENT | % w/w | grams |
|---|---|---|
| HPMC (Methocel E15) | 26.80 | 67.00 |
| LACTOSE | 40.20 | 100.50 |
| PEG 4000 | 8.00 | 20.00 |
| TiO2 | 24.00 | 60.00 |
| IRON OXIDE YELLOW | 1.00 | 2.50 |
| | 100.00 | 250.00 |

EXAMPLE 9

| COMPONENT | % w/w | grams |
|---|---|---|
| HPMC (Methocel E15) | 26.80 | 67.00 |
| LACTOSE | 40.20 | 100.50 |
| PEG 4000 | 8.00 | 20.00 |
| TiO2 | 1.00 | 2.50 |
| INDIGO CARMINE ALUMINUM LAKE 14% | 24.00 | 60.00 |
| | 100.00 | 250.00 |

EXAMPLE 10

| COMPONENT | % w/w | grams |
|---|---|---|
| HPMC (Methocel E15) | 26.80 | 67.00 |
| LACTOSE | 40.20 | 100.50 |
| PEG 400 | 8.00 | 20.00 |
| TiO2 | 24.00 | 60.00 |
| INDIGO CARMINE ALUMINUM LAKE 14% | 1.00 | 2.50 |
| | 100.00 | 250.00 |

EXAMPLE 11

| COMPONENT | % w/w | grams |
|---|---|---|
| HPMC (Methocel E15) | 26.80 | 67.00 |
| LACTOSE | 40.20 | 100.50 |
| PROPYLENE GLYCOL | 8.00 | 20.00 |
| TiO2 | 24.00 | 60.00 |
| INDIGO CARMINE ALUMINUM LAKE 14% | 1.00 | 2.50 |
| | 100.00 | 250.00 |

EXAMPLE 12

| COMPONENT | % w/w | grams |
|---|---|---|
| HPMC (Methocel E15) | 26.80 | 67.00 |
| LACTOSE | 40.20 | 100.50 |
| GLYCEROL | 8.00 | 20.00 |
| TiO2 | 24.00 | 60.00 |
| INDIGO CARMINE ALUMINUM LAKE 14% | 1.00 | 2.50 |
| | 100.00 | 250.00 |

EXAMPLE 13

| COMPONENT | % w/w | grams |
|---|---|---|
| HPC (Klucel EF) | 26.80 | 67.00 |
| LACTOSE | 40.20 | 100.50 |
| PEG 4000 | 8.00 | 20.00 |
| TiO2 | 24.00 | 60.00 |
| INDIGO CARMINE ALUMINUM LAKE 14% | 1.00 | 2.50 |
| | 100.00 | 250.00 |

EXAMPLE 14

| COMPONENT | % w/w | grams |
|---|---|---|
| HPMC (Methocel E50) | 20.83 | 52.07 |
| LACTOSE | 41.67 | 104.17 |
| PEG 4000 | 6.25 | 15.63 |
| TiO2 | 30.00 | 75.00 |
| INDIGO CARMINE ALUMINUM LAKE 14% | 1.25 | 3.13 |
| | 100.00 | 250.00 |

EXAMPLE 15

| COMPONENT | % w/w | grams |
|---|---|---|
| HPMC (Methocel E15) | 26.80 | 67.00 |
| LACTOSE | 40.20 | 100.50 |
| PEG 8000 | 8.00 | 20.00 |
| TiO2 | 24.00 | 60.00 |
| TARTRAZINE ALUMINUM LAKE 25% | 1.00 | 2.50 |
| | 100.00 | 250.00 |

EXAMPLE 16

| COMPONENT | % w/w | grams |
|---|---|---|
| HPMC (Methocel E15) | 26.80 | 67.00 |
| LACTOSE | 40.20 | 100.50 |
| PEG 20,000 | 8.00 | 20.00 |
| TiO2 | 24.00 | 60.00 |
| INDIGO CARMINE ALUMINUM LAKE 14% | 1.00 | 2.50 |
| | 100.00 | 250.00 |

EXAMPLE 17

| COMPONENT | % w/w | grams |
|---|---|---|
| HPMC (Methocel E15) | 26.80 | 67.00 |
| LACTOSE | 40.20 | 100.50 |
| PEG 200 | 8.00 | 20.00 |
| TiO2 | 24.00 | 60.00 |
| INDIGO CARMINE ALUMINUM LAKE 14% | 1.00 | 2.50 |
| | 100.00 | 250.00 |

Examples 18–20 illustrate additional formulations of the dry film coating composition of the invention.

EXAMPLE 18

A dry film coating composition having the following formula is made as in example 1, except that no plasticizer is blended into the composition:

| COMPONENT | % w/w | grams |
|---|---|---|
| HPMC (Methocel E15) | 29.13 | 72.82 |
| LACTOSE | 43.70 | 109.25 |
| TiO2 | 26.08 | 65.20 |
| INDIGO CARMINE ALUMINUM LAKE 14% | 1.09 | 2.73 |
| | 100.00 | 250.00 |

EXAMPLE 19

A dry film coating composition having the following formula is made as in example 1, except that no pigment is blended into the composition:

| COMPONENT | % w/w | grams |
|---|---|---|
| HPMC (Methocel E15) | 35.73 | 89.33 |
| LACTOSE | 53.60 | 133.99 |
| PEG 4000 | 10.67 | 26.68 |
| | 100.00 | 250.00 |

EXAMPLE 20

A dry film coating composition having the following formula is made as in Example 1, except that no plasticizer and no pigment are blended into the composition:

| COMPONENT | % w/w | grams |
|---|---|---|
| HPMC (Methocel E15) | 40.00 | 100.00 |
| LACTOSE | 60.00 | 150.00 |
| | 100.00 | 250.00 |

Each of the dry film coating compositions of Examples 1–20 is constituted in water to form a coating suspension. In each case, 170 grams of the dry film coating composition is dispersed into 830 grams of purified water. Preferably, this is accomplished by placing the 830 grams of purified water into a mixing vessel having the diameter that is about equal to the depth of the final suspension. Then, a low shear mixer is lowered into the water and turned on. Preferably, the mixing head of the mixer is about one third the diameter of the mixing vessel and creates a vortex from the edge of the vessel down to just above the mixing head. The 170 grams of the dry film coating composition is then added to the vortex at a rate where there is no excessive build-up of the dry film coating composition. The speed and depth of the mixing head is adjusted to avoid air being drawn into the suspension which would result in foaming. The suspension is stirred for 45 minutes and is then ready for spraying.

The inventive coating suspensions are then sprayed onto medicinal tablets, vitamin tablets, aspirin tablets, capsules, chewing gum balls, candy pieces, breakfast cereals, and agricultural seeds, and allowed to dry. The film coatings so produced have an excellent appearance and adhere extremely well to the substrates.

Preferably, the inventive film coating suspension is formed by blending together all the dry ingredients of the coating formula, and then dispersing the mixture of the dry ingredients into water. However, the film coating suspension may be prepared by stirring the ingredients of the coating formulation one by one into water to form a coating suspension.

Further, the inventive coating suspension may be spray-granulated to form a dry edible film coating composition that may be remixed into water when desired to form a coating suspension.

The inclusion of lactose in the coating composition dramatically and unexpectedly improves adhesion of the film coating onto substrates such as pharmaceuticals, food, confectionery forms, agricultural seeds, and the like.

The dry film coating composition of the invention when constituted in water has a viscosity lower than that of a conventional polymer coating system having the same total solids. For an equivalent final dispersion viscosity as a conventional polymer coating system, a coating dispersion may be produced under the invention which has a higher solids loading, and consequently a lower solvent content. Accordingly, since the film coating suspensions of the invention may be sprayed at a higher solids level, spraying times are lower than the spraying times for conventional systems, which results in lower processing time cost.

Most cellulosic polymers show some degree of tack as they dry on the substrate surface. This tack is reduced with the inclusion of lactose in the inventive formula, thus further facilitating faster processing times, and thereby lowering costs.

The inclusion of lactose in the inventive formulation improves the light stability of organic pigments and natural colors commonly used in film coatings.

The inclusion of lactose in the formulation has the effect of reducing the moisture vapor permeability of the film.

I claim:

1. A dry film coating composition for forming a coating suspension for film coating pharmaceuticals, food, confectionery forms, and agricultural seeds, comprising
   a cellulosic polymer, and
   lactose,
   the cellulosic polymer being from 11% to 56% by weight of the composition,
   the lactose being from 11% to 56% by weight of the composition.

2. A dry film composition according to claim 1, further comprising
   a plasticizer.

3. A dry film coating composition according to claim 2, in which
   the plasticizer is polyethylene glycol of a molecular weight between 200 to 20,000, propylene glycol, or glycerol.

4. A dry film coating composition according to claim 2, in which
   the plasticizer is greater than 0% to 30% by weight of the composition.

5. The dry film coating composition of claim 2,
   the plasticizer being 5% to 20% by weight of the composition.

6. The dry film coating composition of claim 1,
   the lactose being 25% to 45% by weight of the composition.

7. A dry film coating composition of claim 1, further comprising
   a pigment.

8. A dry film coating composition according to claim 7, in which
   the pigment is selected from the group consisting of FD&C lakes, D&C lakes, natural pigments, and combinations thereof.

9. A dry film coating composition according to claim 7 in which
   the pigment is greater than 0% to 55% by weight of the composition.

10. The dry film coating composition of claim 2,
    the pigment being 15% to 40% by weight of the composition.

11. A dry film coating composition of claim 1 in which,
    the cellulosic polymer is hydroxypropyl methylcellulose or hydroxypropyl cellulose.

12. A dry film coating composition of claim 1, in which
    the cellulosic polymer is from 20% to 30% by weight of the composition.

13. A dry film coating composition for forming a coating suspension for film coating pharmaceuticals, food, confectionery forms, and agricultural seeds, comprising a cellulosic polymer, lactose, a plasticizer, and a pigment, the cellulosic polymer being 20% to 30% by weight of the composition, the cellulosic polymer being hydroxypropyl methylcellulose or hydroxypropyl cellulose, the lactose being 25% to 45% by weight of the composition, the plasticizer being 5% to 20% by weight of the composition, the plasticizer being polyethylene glycol of a molecular weight between 200 to 20,000, propylene glycol, or glycerol, the pigment being 15% to 40% by weight of the composition, and the pigment being FD&C lakes, D&C lakes, or natural pigments.

14. A film coating for pharmaceuticals, food, confectionery forms, and agricultural seeds, comprising a cellulosic polymer, and lactose, the lactose being from 11% to 56% by weight of the film coating, the cellulosic polymer being 11% to 56% by weight of the film coating.

15. The film coating of claim 14, further comprising a plasticizer.

16. The film coating of claim 14, further comprising a pigment.

17. The film coating of claim 14, the cellulosic polymer being from 20% to 30% by weight of the film coating.

18. The coating composition of claim 14, the lactose being from 25% to 45% by weight of the film coating.

19. The film coating of claim 14, further including, a plasticizer, and a pigment, the cellulosic polymer being 20% to 30% by weight of the film coating, the cellulosic polymer being hydroxypropyl methylcellulose or hydroxypropyl cellulose, the lactose being 25% to 45% by weight of the composition, the plasticizer being 5% to 20% by weight of the composition, the plasticizer being polyethylene glycol of a molecular weight between 200 to 20,000, propylene glycol, or glycerol, the pigment being 15% to 40% by weight of the composition, and the pigment being FD&C lakes, D&C lakes, or natural pigments.

* * * * *